United States Patent
Do et al.

(10) Patent No.: US 9,434,752 B2
(45) Date of Patent: *Sep. 6, 2016

(54) DINUCLEAR METALLOCENE COMPOUND, AND A METHOD FOR PREPARING THE SAME

(71) Applicant: LG CHEM, LTD., Seoul (KR)

(72) Inventors: Young Shil Do, Daejeon (KR); Choong Hoon Lee, Daejeon (KR); Seung Hwan Jung, Daejeon (KR); Ji Joong Moon, Daejeon (KR); Yoon Hee Cho, Daejeon (KR); Sang Eun Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/895,875

(22) PCT Filed: Dec. 27, 2013

(86) PCT No.: PCT/KR2013/012320
§ 371 (c)(1),
(2) Date: Dec. 3, 2015

(87) PCT Pub. No.: WO2014/208852
PCT Pub. Date: Dec. 31, 2014

(65) Prior Publication Data
US 2016/0108069 A1    Apr. 21, 2016

(30) Foreign Application Priority Data

Jun. 25, 2013  (KR) .................. 10-2013-0073043
Dec. 27, 2013  (KR) .................. 10-2013-0165067

(51) Int. Cl.
*C07F 7/28*      (2006.01)
*C07F 7/00*      (2006.01)
*C07F 17/00*     (2006.01)
*C08F 4/76*      (2006.01)

(52) U.S. Cl.
CPC .............. *C07F 7/28* (2013.01); *C07F 17/00* (2013.01); *C08F 4/76* (2013.01)

(58) Field of Classification Search
USPC ............................ 546/10; 548/402
See application file for complete search history.

(56) References Cited

U.S. PATENT DOCUMENTS

| | | |
|---|---|---|
| 5,032,562 A | 7/1991 | Lo et al. |
| 6,153,776 A | 11/2000 | Patton et al. |
| 6,288,254 B1 | 9/2001 | Chen et al. |
| 7,928,256 B2 | 4/2011 | Lee et al. |
| 8,039,671 B2 | 10/2011 | Lee et al. |
| 8,048,973 B2 | 11/2011 | Lee et al. |

FOREIGN PATENT DOCUMENTS

| | | |
|---|---|---|
| JP | 2000-169492 A | 6/2000 |
| KR | 10-2000-0025587 A | 5/2000 |
| KR | 10-2004-0076965 A | 9/2004 |
| KR | 10-2007-0079254 A | 8/2007 |
| KR | 10-2007-0096465 A | 10/2007 |
| KR | 10-2008-0076187 A | 8/2008 |
| KR | 10-2008-0104562 A | 12/2008 |
| KR | 10-2009-0063799 A | 6/2009 |
| KR | 10-2010-0067627 A | 6/2010 |
| KR | 10-2012-0028269 A | 3/2012 |
| KR | 10-2012-0029162 A | 3/2012 |
| KR | 10-2015-0000813 A | 1/2015 |

OTHER PUBLICATIONS

Marc Schilling, et al. Dinuclear metallocene complexes as catalyst precurs ors for homogeneous ethylene polymerization. Applied Catalysis A: General, vol. 348, pp. 79-85 (2008).
Swadhin K. Mandal, et al., Oxygen-Bridged Hybrid Metallocene-Nonmetallocene Polymetallic Catalysts of Group 4 Metals for Bimodal Activity in Olefin Polymerization: Synthesis, Characterization, and Theoretical Investigation. Inorg. Chem. 2007, 46, 10158-10167.
Prabhuodeyara M. Gurubasavaraj, et al., Oxygen Effect in Heterobimetallic Catalysis: The Zr—O—Ti System as an Excellent Example for Olefin Polymerization. Organometallics 2007, 26, 3346-3351.
Min Hyung Lee et al., Biphenylene-Bridged Dinuclear Group 4 Metal Complexes: Enhanced Polymerization Properties in Olefin Polymerization. Organometallics 2005, 24, 3618-3620.
Feng Lin et al., Ethylene Polymerization by 3-oxa-pentamethylene bridged dinuclear metallocene (Ti, Zr)/MAO Systems. Eur. Polym, J.I 43, 1436-1443 (2007).

*Primary Examiner* — Charanjit Aulakh
(74) *Attorney, Agent, or Firm* — Dentons US LLP

(57) ABSTRACT

The present invention relates to a dinuclear metallocene compound with a new structure which can manufacture polyolefin having high molecular weight and to a method for preparing the same. The dinuclear metallocene compound according to the present invention is a dinuclear metallocene compound with a new structure, and, unlike a single-site catalyst, has high accessibility to a substrate, and thus, can provide a multi-site catalyst with high activity.

5 Claims, No Drawings

DINUCLEAR METALLOCENE COMPOUND, AND A METHOD FOR PREPARING THE SAME

This application is a National Stage Application of International Application No. PCT/KR2013/012320, filed Dec. 27, 2013, and claims priority to and the benefit of Korean Patent Application No. 10-2013-0073043, filed on Jun. 25, 2013, and Korean Patent Application No. 10-2013-0165067, filed on Dec. 27, 2013 the contents of each which is incorporated by reference in its entirety for all purposes as if fully set forth below.

BACKGROUND OF THE INVENTION (a) Field of the Invention

The present invention relates to a dinuclear metallocene compound, and a method for preparing the same. More specifically, the present invention relates to a dinuclear metallocene compound with a novel structure which can prepare polyolefin having high molecular weight, and a method for preparing the same.

(b) Description of the Related Art

Since a Zeigler-Natta catalyst widely applied in an industrial process is a multi-site catalyst, the molecular weight distribution of the produced polymer is wide, and the composition distribution of comonomers is not uniform, and thus, has a limitation in securing desired properties.

Meanwhile, a metallocene catalyst is a single-site catalyst having one kind of an active site, and it has advantages in that the molecular weight distribution of the produced polymer is narrow, and that the molecular weight, stereoregularity, crystallinity, particularly reactivity of comonomers may be greatly controlled according to the structure of the catalyst and the ligand. However, polyolefin polymerized using a metallocene catalyst has narrow molecular weight distribution, and if applied for some products, productivity is remarkably decreased due to extrusion load and the like, rendering site application difficult, and thus, there have been many attempts to control the molecular weight distribution of polyolefin For this, a method of using a mononuclear metallocene compound and a dinuclear metallocene compound is known.

As an example of the mononuclear metallocene compound, U.S. Pat. No. 5,032,562 describes a method of preparing a polymerization catalyst by supporting two different transition metal catalysts on one carrier. This is a method of producing bimodal distribution polymer by supporting a titanium (Ti)-based Ziegler Natta catalyst producing high molecular weight and a zirconium (Zr)-based metallocene catalyst producing low molecular weight on one carrier, however, it has disadvantages in that the supporting process is complicated, and the morphology of polymer becomes worse due to a cocatalyst.

And, studies on changing copolymer selectivity and activity of a catalyst in copolymerization using a dinuclear metallocene compound has been reported, and in case of some metallocene catalysts, copolymer incorporation and activity increase have been reported.

For example, Korean Patent Application No. 2003-12308 discloses a method of controlling molecular weight distribution by supporting a dinuclear metallocene catalyst and a mononuclear metallocene catalyst on a carrier together with an activator and polymerizing while changing the combination of catalysts in the reactor. However, this method has a limitation in simultaneously realizing the properties of each catalyst, and has a disadvantage in that a metallocene catalyst part is dissociated in the carrier component of the final catalyst, thus causing fouling of a reactor.

And, a synthesis method of a Group 4 metallocene catalyst having a biphenylene bridge and polymerization of ethylene and styrene using the same have been reported (Organometallics, 2005, 24, 3618). According to this method, it is stated that catalytic activity is high and the molecular weight of the obtained polymer is high, compared to a mononuclear metallocene catalyst. It has been also reported that reactivity of a catalyst may be changed by converting the bridge structure of Group 4 dinuclear metallocene catalyst (Eur. Polym, J. 2007, 43, 1436).

However, if using these methods, previously reported Group 4 metallocene catalyst having a biphenylene bridge has problems in terms of addition of substituents and modification of a structure. Therefore, there is a need for development of novel metallocene catalyst useful for preparation of olefin.

SUMMARY OF THE INVENTION

In order to solve the above problem, it is an object of the invention to provide a novel dinuclear metallocene compound, which can prepare polyolefin having high molecular weight with high activity.

It is another object of the invention to provide a method for preparing the dinuclear metallocene compound.

In order to achieve the objects, one aspect of the invention provides a dinuclear metallocene compounds represented by the following Chemical Formula 1:

[Chemical Formula 1]

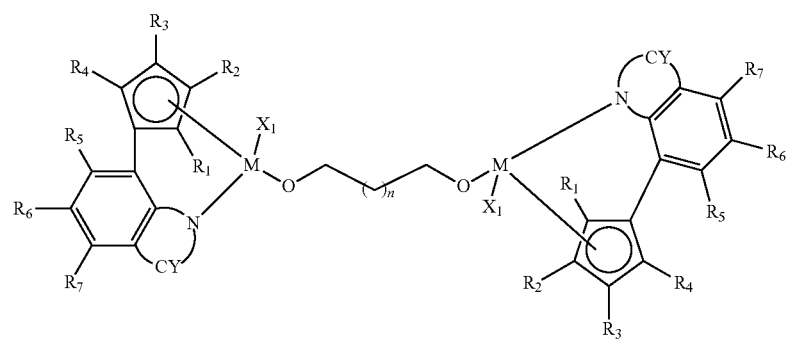

in the Chemical Formula 1,

R1 to R4 may be identical to or different from each other, and are independently hydrogen; a halogen radical; an alkyl radical having a carbon number of 1 to 20; an alkenyl radical having a carbon number of 2 to 20; a silyl radical; an aryl radical having a carbon number of 6 to 20; an alkylaryl radical having a carbon number of 7 to 20; or an arylalkyl radical having a carbon number of 7 to 20; and two or more adjacent radicals of R1 to R4 may be linked each other to form an aliphatic ring, or an aromatic ring;

R5 to R7 may be identical to or different from each other, and are independently hydrogen; a halogen radical; an alkyl radical having a carbon number of 1 to 20; an alkenyl radical having a carbon number of 2 to 20; an aryl radical having a carbon number of 6 to 20; an alkylaryl radical having a carbon number of 7 to 20; an arylalkyl radical having a carbon number of 7 to 20; an alkoxy radical having a carbon number of 1 to 20; an aryloxy radical having a carbon number of 6 to 20; or an amido radical; and two or more adjacent radicals of R5 to R7 may be linked each other to form an aliphatic ring, or an aromatic ring;

CY is an aliphatic or aromatic ring containing nitrogen, and may be unsubstituted or substituted with halogen, an alkyl or aryl radical having a carbon number of 1 to 20, and if it has multiple substituents, two or more substituents may be linked each other to form an aliphatic or aromatic ring;

M is Group 4 transition metal;

X1 is a halogen radical; an alkyl radical having a carbon number of 1 to 20; an alkenyl radical having a carbon number of 2 to 20; an aryl radical having a carbon number of 6 to 20; an alkylaryl radical having a carbon number of 7 to 20; an arylalkyl radical having a carbon number of 7 to 20; an alkylamido radical having a carbon number of 1 to 20; an arylamido radical having a carbon number of 6 to 20; or an alkylidene radical having a carbon number of 1 to 20; and n is an integer of 0 to 10.

Another aspect of the invention provides a method for preparing the dinuclear metallocene compound.

The dinuclear metallocene compound according to the present invention is a novel dinuclear metallocene compound, and the dinuclear metallocene compound has high accessibility to a substrate unlike a single-site catalyst Thus, the present invention can provide a multi-site catalyst with high activity.

And, using the catalyst of the present invention, polyolefin having high molecular weight can be produced.

DETAILED DESCRIPTION OF THE EMBODIMENTS

As used herein, terms "a first", "a second" and the like are used to explain various constructional elements, and they are used only to distinguish one constructional element from other constructional elements.

And, the terms used herein are only to explain illustrative examples, and are not intended to limit the invention. A singular expression includes a plural expression thereof, unless it is expressly stated or obvious from the context that such is not intended. As used herein, the terms "comprise", "contain" or "have" and the like are intended to designate the existence of practiced characteristic, number, step, constructional element or combinations thereof, and they are not intended to preclude the possibility of existence or addition of one or more other characteristics, numbers, steps, constructional elements or combinations thereof.

And, in case it is stated that each constructional element is formed "on" or "above" each construction element, it means that each constructional element is formed directly on each constructional element, or that other constructional elements may be additionally formed between the layers or on the object or substrate.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, the present invention will be explained in detail.

According to one aspect of the invention, provided is a dinuclear metallocene compounds represented by the following Chemical Formula 1:

[Chemical Formula 1]

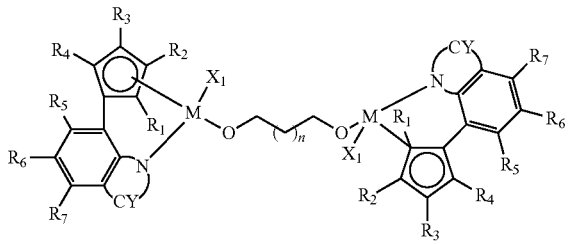

in the Chemical Formula 1,

R1 to R4 may be identical to or different from each other, and are independently hydrogen; a halogen radical; an alkyl radical having a carbon number of 1 to 20; an alkenyl radical having a carbon number of 2 to 20; a silyl radical; an aryl radical having a carbon number of 6 to 20; an alkylaryl radical having a carbon number of 7 to 20; or an arylalkyl radical having a carbon number of 7 to 20; and two or more adjacent radicals of R1 to R4 may be linked each other to form an aliphatic ring, or an aromatic ring;

R5 to R7 may be identical to or different from each other, and are independently hydrogen; a halogen radical; an alkyl radical having a carbon number of 1 to 20; an alkenyl radical having a carbon number of 2 to 20; an aryl radical having a carbon number of 6 to 20; an alkylaryl radical having a carbon number of 7 to 20; an arylalkyl radical having a carbon number of 7 to 20; an alkoxy radical having a carbon number of 1 to 20; an aryloxy radical having a carbon number of 6 to 20; or an amido radical; and two or more adjacent radicals of R5 to R7 may be linked each other to form an aliphatic ring, or an aromatic ring;

CY is an aliphatic or aromatic ring containing nitrogen, and may be unsubstituted or substituted with halogen, an alkyl or aryl radical having a carbon number of 1 to 20, and if it has multiple substituents, two or more substituents may be linked each other to form an aliphatic or aromatic ring;

M is Group 4 transition metal;

X1 is a halogen radical; an alkyl radical having a carbon number of 1 to 20; an alkenyl radical having a carbon number of 2 to 20; an aryl radical having a carbon number of 6 to 20; an alkylaryl radical having a carbon number of 7 to 20; an arylalkyl radical having a carbon number of 7 to 20; an alkylamido radical having a carbon number of 1 to 20; an arylamido radical having a carbon number of 6 to 20; or an alkylidene radical having a carbon number of 1 to 20; and n is an integer of 0 to 10.

According to one embodiment of the invention, in the dinuclear metallocene compound of the Chemical Formula 1, R1 to R7 are independently hydrogen, an alkyl group having a carbon number of 1 to 20, or an aryl group having a carbon number of 6 to 20, or two or more adjacent radicals of R1 to R7 may be linked each other to form one or more aliphatic ring, or aromatic ring, but the present invention is not limited thereto.

And, CY may be a pentagonal or hexagonal aliphatic or aromatic ring containing nitrogen, unsubstituted or substituted with an alkyl group having a carbon number of 1 to 20, but the present invention is not limited thereto.

And, M may be titanium (Ti), zirconium (Zr), or hafnium (Hf), and X1 may be halogen or an alkyl group having a carbon number of 1 to 20, but the present invention is not limited thereto.

The dinuclear metallocene compound represented by the Chemical Formula 1 includes a structure wherein two single metallocene compounds respectively bridged with a phenylene group having a cyclic amido group introduced therein are crosslinked by alkylenedioxy (—O—(CH$_2$)—(CH$_2$)n-(CH$_2$)—O—). Thus, two metal centers are connected by a diether chain functioning as a linker, to reduce unnecessary interactions between the metals, thus affording stable catalytic activity and easiness of structural deformation, and unlike a single-site catalyst, the compound has high accessibility to a substrate and thus exhibits high activity. Thus, by using the dinuclear metallocene compound as a catalyst for polymerization or copolymerization of polyolefin, polyolefin having high molecular weight and wide molecular weight distribution can be produced with high activity. And, various substituents may be introduced into the cyclopentadienyl and the cyclic amido ring such as quinoline or indoline, which ultimately enables easy controlling of electronic, steric environment around the metals. Namely, by using the compound with such a structure, the structure and properties and the like of prepared olefin polymer may be easily controlled.

Examples of the dinuclear metallocene compound represented by the Chemical Formula 1 include the following compounds, but are not limited thereto.

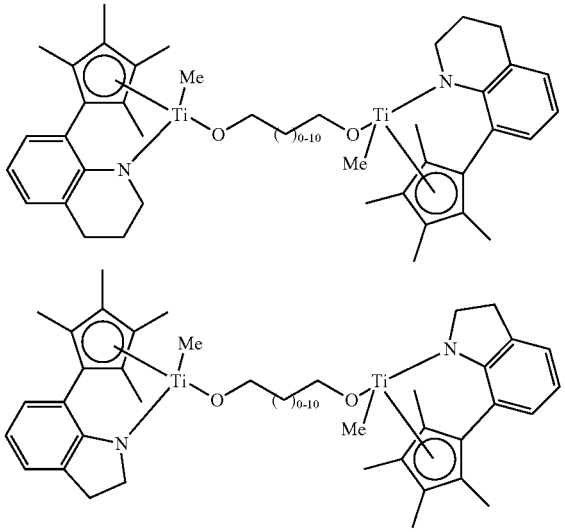

According to another aspect of the invention, provided is a method for preparing a dinuclear metallocene compound represented by the following Chemical Formula 1, comprising a step of reacting a compound represented by the following Chemical Formula 2 with a compound represented by the following Chemical Formula 3:

[Chemical Formula 1]

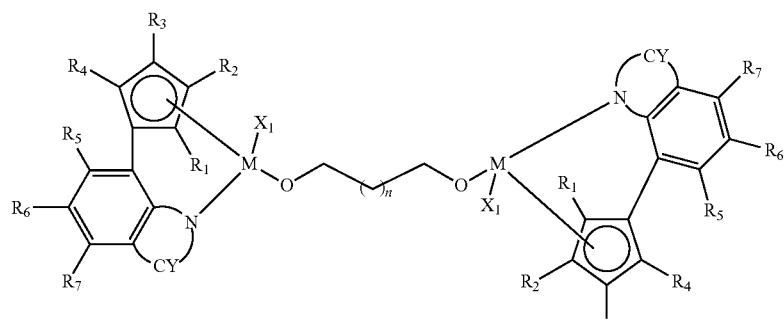

[Chemical Formula 2]

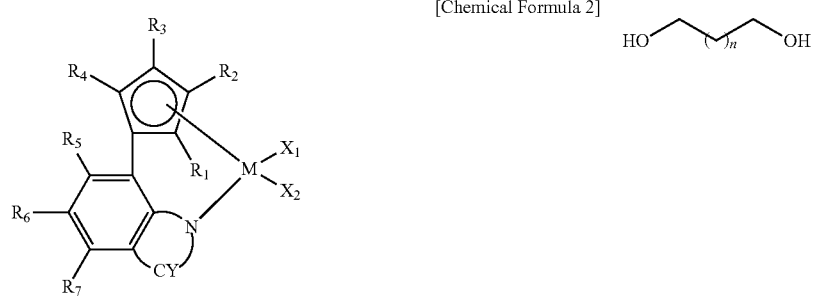

[Chemical Formula 3]

in the Chemical Formulae 1, 2 and 3,

R1 to R4 may be identical to or different from each other, and are independently hydrogen; a halogen radical; an alkyl radical having a carbon number of 1 to 20; an alkenyl radical having a carbon number of 2 to 20; a silyl radical; an aryl radical having a carbon number of 6 to 20; an alkylaryl radical having a carbon number of 7 to 20; or an arylalkyl radical having a carbon number of 7 to 20; and two or more adjacent radicals of R1 to R4 may be linked each other to form an aliphatic ring, or an aromatic ring;

R5 to R7 may be identical to or different from each other, and are independently hydrogen; a halogen radical; an alkyl radical having a carbon number of 1 to 20; an alkenyl radical having a carbon number of 2 to 20; an aryl radical having a carbon number of 6 to 20; an alkylaryl radical having a carbon number of 7 to 20; an arylalkyl radical having a carbon number of 7 to 20; an alkoxy radical having a carbon number of 1 to 20; an aryloxy radical having a carbon number of 6 to 20; or an amido radical; and two or more adjacent radicals of R5 to R7 may be linked each other to form an aliphatic ring, or an aromatic ring;

CY is an aliphatic or aromatic ring containing nitrogen, and may be unsubstituted or substituted with halogen, an alkyl or aryl radical having a carbon number of 1 to 20, and if it has multiple substituents, two or more substituents may be linked each other to form an aliphatic or aromatic ring;

M is Group 4 transition metal;

X1 and X2 may be identical to or different from each other, and are independently a halogen radical; an alkyl radical having a carbon number of 1 to 20; an alkenyl radical having a carbon number of 2 to 20; an aryl radical having a carbon number of 6 to 20; an alkylaryl radical having a carbon number of 7 to 20; an arylalkyl radical having a carbon number of 7 to 20; an alkylamido radical having a carbon number of 1 to 20; an arylamido radical having a carbon number of 6 to 20; or an alkylidene radical having a carbon number of 1 to 20; and n is an integer of 0 to 10.

The method for preparing a dinuclear metallocene compound may be conducted by mixing the mononuclear metallocene compound represented by the Chemical Formula 2 with the diol compound represented by the Chemical Formula 3, and then, stirring for a certain time. The stirring temperature may be about −30 to about 25° C., preferably room temperature, and the stirring time may be 12 hours or more, for example, about 12 hours to about 36 hours, but not limited thereto. And, the stirring may be conducted in an organic solvent such as MTBE (methyl tertiary-butyl ether) or toluene, and a dinuclear metallocene compound may be obtained by extracting in n-hexane, but the preparation method of the invention is not limited thereto.

The diol compound represented by the Chemical Formula 3 may react at 0.5 equivalents to the mononuclear metallocene compound represented by the Chemical Formula 2.

The dinuclear metallocene compound represented by the Chemical Formula 1 may be prepared according to any methods known in the technical field to which the invention pertains, without specific limitations.

The method for preparing a dinuclear metallocene compound represented by the Chemical Formula 1 will be illustrated and explained in detail in the examples below.

According to the preparation method of the present invention, a dinuclear metallocene compound represented by the Chemical Formula 1 may be prepared by a simple process under relatively mild conditions, and by controlling the distance between dinuclear active sites according to the length of the alkyl chain of a diol compound, activity may be easily controlled while reducing unnecessary interactions. And, the compound has stable catalytic activity and the structural deformation is easy, and unlike a single-site catalyst, it has high accessibility to a substrate and thus exhibits high activity.

The dinuclear metallocene compound represented by the Chemical Formula 1 may be used as a catalyst composition alone or in combination with a cocatalyst to prepare polyolefin polymer, and particularly, it may produce polyolefin having high molecular weight with high activity. For example, a catalyst composition comprising the dinuclear metallocene compound represented by the Chemical Formula 1 may be contacted with monomers to conduct a polymerization process, thereby providing olefin homopolymer or olefin copolymer.

Hereinafter, the actions and the effects of the invention will be explained in detail, with reference to specific examples. However, these examples are only presented to illustrate the invention, and the right scope of the invention is not determined thereby.

EXAMPLE

The organic reagents and solvents used in the following examples, unless specifically mentioned, were purchased from Aldrich Company, purified by a standard method and used. In all the synthesis steps, contact of air with moisture was blocked to increase reproducibility of the experiments.

Synthesis of Dinuclear Metallocene Compound

Example 1

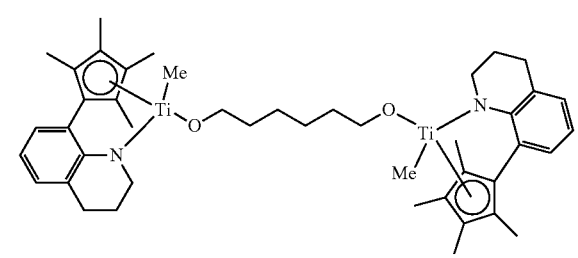

([(1,2,3,4-tetrahydroquinolin-8-yl)tetramethylcyclopentadienyl-eta5, kappa-N]titanium dimethyl) (1 g, 3.04 mmol) was dissolved in a methyl tertiary-butyl ether (40 mL) solvent. And then, it was slowly added dropwise to a solution of 1,6-hexanediol (180 mg, 1.52 mmol) dissolved in methyl tertiary-butyl ether (20 mL) at −20° C. The temperature of an orange solution was slowly raised and the solution was stirred at room temperature (25° C.) for 36 hours.

After removing the methyl tertiary-butyl ether solvent, 30 ml of n-hexane was added to filter, and then, a desired compound in the form of orange solid was obtained (1.0 g, 95% or more yield).

$^1$H NMR (CDCl$_3$): δ 1.26 (s, 3H, Ti—CH$_3$), 1.85 (m, 6H, Cp-CH$_3$), 1.00~2.00 (br, 6H, diol aliphatic (CH$_2$)$_2$, quinoline-CH$_2$), 2.13 (m, 6H, Cp-CH$_3$ and CH$_3$), 2.61 (m, 2H, quinoline-CH$_2$), 3.77 (br, 2H, OCH$_2$), 4.16 (m, 2H, quinoline-NCH$_2$), 6.64 (m, 1H, aromatic), 6.91 (m, 2H, aromatic) ppm

Example 2

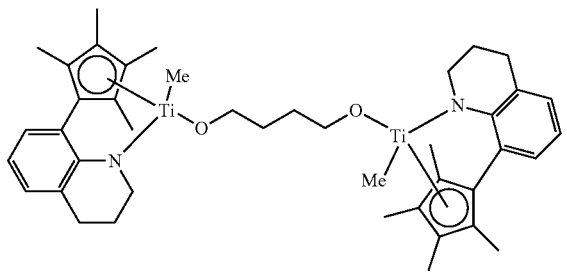

([(1,2,3,4-tetrahydroquinolin-8-yl)tetramethylcyclopentadienyl-eta5, kappa-N]titanium dimethyl) (1 g, 3.04 mmol) was dissolved in a methyl tertiary-butyl ether (40 mL) solvent. And then, it was slowly added dropwise to a solution of 1,4-butanediol (140 mg, 1.55 mmol) dissolved in methyl tertiary-butyl ether (20 mL) at −20° C. The temperature of an orange solution was slowly raised and the solution was stirred at room temperature (25° C.) for 36 hours.

After removing the methyl tertiary-butyl ether solvent, 30 mL of n-hexane was added to filter, and a desired compound in the form of orange solid was obtained (1.0 g, 95% or more yield).

$^1$H NMR (CDCl$_3$): δ 1.26 (s, 3H, Ti—CH$_3$), 1.85 (m, 6H, Cp-CH$_3$), 1.00~2.00 (br, 4H, diol aliphatic (CH$_2$), quinoline-CH$_2$), 2.13 (m, 6H, Cp-CH$_3$ and CH$_3$), 2.62 (m, 2H, quinoline-CH$_2$), 3.79 (br, 2H, OCH$_2$), 4.17 (m, 2H, quinoline-NCH$_2$), 6.64 (m, 1H, aromatic), 6.89 (m, 2H, aromatic) ppm

Example 3

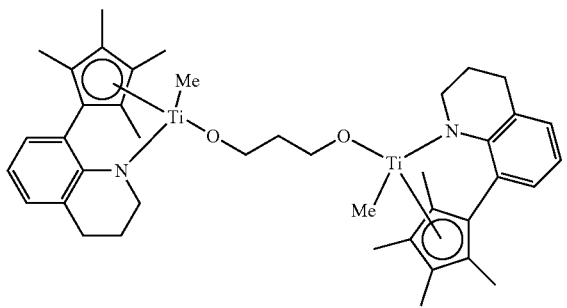

([(1,2,3,4-tetrahydroquinolin-8-yl)tetramethylcyclopentadienyl-eta5, kappa-N]titanium dimethyl) (1 g, 3.04 mmol) was dissolved in a methyl tertiary-butyl ether (40 mL) solvent. And then, it was slowly added dropwise to a solution of 1,3-propanediol (115 mg, 1.51 mmol) dissolved in methyl tertiary-butyl ether (20 mL) at −20° C. The temperature of an orange solution was slowly raised and the solution was stirred at room temperature (25° C.) for 36 hours.

After removing the methyl tertiary-butyl ether solvent, 30 mL of n-hexane was added to filter, and a desired compound in the form of orange solid was obtained (1.0 g, 95% or more yield).

$^1$H NMR (CDCl$_3$): δ 1.19 (s, 3H, Ti—CH$_3$), 1.84 (m, 6H, Cp-CH$_3$), 1.00~2.00 (br, 4H, diol aliphatic (CH$_2$), quinoline-CH$_2$), 2.01 (m, 6H, Cp-CH$_3$ and CH$_3$), 2.61 (m, 2H, quinoline-CH$_2$), 3.97 (br, 2H, OCH$_2$), 4.24 (m, 2H, quinoline-NCH$_2$), 6.71 (m, 1H, aromatic), 6.90 (m, 2H, aromatic) ppm

Comparative Example 1

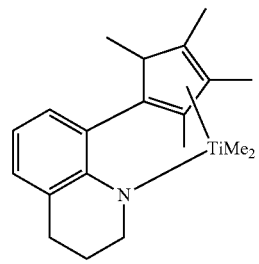

A compound of the above structural formula was prepared according to the method described in Example 7 of US 20070025158A1.

Preparation of Olefin Copolymer

Experimental Example 1

Into a 2 L autoclave reactor, a hexane solvent (1.0 L) and 6.4 mmol of 1-octene were added, and then, the temperature of the reactor was preheated to 120° C. To a 25 mL catalyst storage tank, the compound of Example 1 (0.5 μmol) treated with triisobutylaluminum (10 μmol) and a dimethylanilinium tetrakis(pentafluorophenyl)borate cocatalyst (10 μmol) were sequentially added and filled (the mole ratio of Al:Ti is 10). Subsequently, ethylene pressure (35 bar) was added into the autoclave reactor, and a catalyst composition was injected into the reactor using high pressure argon gas to progress copolymerization for 10 minutes. Next, the remaining ethylene gas was taken out and a polymer solution was added to an excessive amount of ethanol to induce precipitation. The precipitated polymer was washed with ethanol and acetone each two or three times, and dried in a 80° C. vacuum oven for 12 hours or more, and then, the properties were measured.

Experimental Example 2

Into a 2 L autoclave continuous process reactor, a hexane solvent (4.53 kg/h) and 1-octene (0.8 kg/h) were filled, and then, the temperature of the upper part of the reactor was preheated to 150° C. Triisobutylaluminium (0.05 mmol/min), the compound of Example 1 (0.5 μmol/min), and a dimethylanilinium tetrakis(pentafluorophenyl)borate cocatalyst (1.5 μmol/min) were simultaneously introduced into the reactor.

Subsequently, ethylene (0.84 kg/h) was introduced into the autoclave reactor, and the same temperature was maintained for 30 minutes or more and then copolymerization was progressed for 8 minutes in a continuous process to obtain copolymer. Next, the remaining ethylene gas was taken out, and the polymer solution was dried in a 80° C. vacuum oven for 12 hours or more, and then, the properties were measured.

Experimental Example 3

Into a 2 L autoclave continuous process reactor, a hexane solvent (5.4 kg/h) and 1-butene (0.8 kg/h) were filled, and then, the temperature of the upper part of the reactor was preheated to 150° C. Triisobutylaluminium (0.05 mmol/min), the compound of Example 1 (0.5 μmol/min), and a dimethylanilinium tetrakis(pentafluorophenyl)borate cocatalyst (1.5 μmol/min) were simultaneously introduced into the reactor.

Subsequently, ethylene (0.83 kg/h) was introduced into the autoclave reactor, and the same temperature was maintained for 30 minutes or more and then copolymerization was progressed for 8 hours in a continuous process to obtain copolymer. Next, the remaining ethylene gas was taken out, and the polymer solution was dried in a 80° C. vacuum oven for 12 hours or more, and then, the properties were measured.

Experimental Example 4

Ethylene-1-octene copolymer was prepared by the same method as Experimental Example 1, except that 0.5 μmol of the compound of Example 2 was introduced instead of the compound of Example 1 in Experimental Example 1.

Experimental Example 5

Ethylene-1-octene copolymer was prepared by the same method as Experimental Example 2, except that the compound of Example 2 (0.5 μmol/min) was introduced instead of the compound of Example 1 in Experimental Example 2.

Experimental Example 6

Ethylene-1-butene copolymer was prepared by the same method as Experimental Example 3, except that the compound of Example 2 (0.5 μmol/min) was introduced instead of the compound of Example 1 in Experimental Example 3.

Experimental Example 7

Ethylene-1-octene copolymer was prepared by the same method as Experimental Example 1, except that 0.5 μmol of the compound of Example 3 was introduced instead of the compound of Example 1 in Experimental Example 1.

Experimental Example 8

Ethylene-1-octene copolymer was prepared by the same method as Experimental Example 2, except that the compound of Example 3 (0.5 μmol/min) was introduced instead of the compound of Example 1 in Experimental Example 2.

Experimental Example 9

Ethylene-1-butene copolymer was prepared by the same method as Experimental Example 3, except that the compound of Example 3 (0.5 μmol/min) was introduced instead of the compound of Example 1 in Experimental Example 3.

Comparative Experimental Example 1

Ethylene-1-octene copolymer was prepared by the same method as Experimental Example 1, except that 1.0 μmol of the compound of Comparative Example 1 was introduced instead of the compound of Example 1 in Experimental Example 1.

Comparative Experimental Example 2

Ethylene-1-octene copolymer was prepared by the same method as Experimental Example 2, except that the compound of Comparative Example 1 (1.0 μmol/min) was introduced instead of the compound of Example 1 in Experimental Example 2.

Comparative Experimental Example 3

Ethylene-1-butene copolymer was prepared by the same method as Experimental Example 3, except that the compound of Comparative Example 1 (1.0 μmol/min) was introduced instead of the compound of Example 1 in Experimental Example 3.

The catalytic activities and the properties of ethylene-1-octene copolymer in Experimental Example 1 and Comparative Experimental Example 1 are shown in the Table 1 below.

TABLE 1

|  | Experimental Example 1 | Comparative Experimental Example 1 |
|---|---|---|
|  | Catalyst compound | |
|  | Example 1 | Comparative Example 1 |
| Reaction temperature(unit: ° C.) | 120 | 120 |
| Catalyst compound(unit: μmol) | 0.5 | 1.0 |
| Al(cocatalyst):Ti(catalyst compound) mole ratio | 10 | 10 |
| 1-octene introduction amount (unit: mmol) | 6.4 | 6.4 |
| Activity (unit: kgPOE/mmol Ti hr) | 76 | 75 |
| Melt index $I_2$ (unit: g/10 min) | 1.12 | 2.56 |
| Melt index $I_{10}$ (unit: g/10 min) | 11.2 | 29.9 |
| $I_{10}/I_2$ | 10 | 11.7 |
| Density (unit: g/ml) | 0.862 | 0.862 |
| Tm (unit: ° C.) | 44.1 | 41.9 |

And, the catalytic activities and the properties of ethylene-1-octene copolymer in Experimental Example 2 and Comparative Experimental Example 2 are shown in the Table 2 below.

TABLE 2

|  | Experimental Example 2 | Comparative Experimental Example 2 |
|---|---|---|
|  | Catalyst compound | |
|  | Example 1 | Comparative Example 1 |
| Reaction temperature(unit: ° C.) | 150 | 150 |
| Catalyst compound(unit: μmol/min) | 0.5 | 1.0 |
| Al(cocatalyst):Ti(catalyst compound) mole ratio | 50 | 50 |
| 1-octene introduction amount (unit: mmol) | 760 | 760 |
| Yield (unit: g/h) | 1024.2 | 966.0 |
| Activity (unit: kgPE/mmol Ti hr) | 48.8 | 32.2 |
| Melt index $I_2$ (unit: g/10 min) | 4.21 | 3.34 |
| Density (unit: g/ml) | 0.869 | 0.868 |
| Tm (unit: ° C.) | 50.7 | 51.5 |

Referring to Tables 1 and 2, since the dinuclear metallocene compound of the present invention has a structure wherein single metallocene compounds are connected by a diether chain, unnecessary interactions between the metals may be minimized to afford stable catalytic activity, and thus, it has high activity and can prepare polyolefin having high molecular weight compared to mononuclear metallocene catalyst.

What is claimed is:

1. A dinuclear metallocene compound represented by the following Chemical Formula 1:

[Chemical Formula 1]

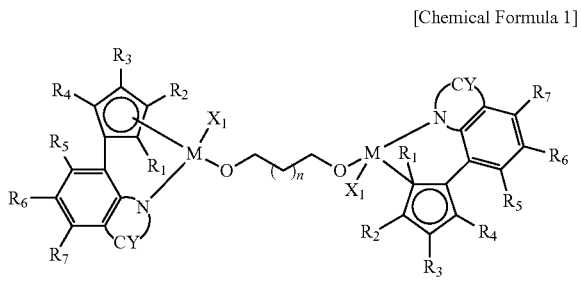

in the Chemical Formula 1,
R1 to R7 are independently hydrogen, an alkyl group having a carbon number of 1 to 20, or an aryl group having a carbon number of 6 to 20;
CY is a pentagonal or hexagonal aliphatic or aromatic ring containing nitrogen, unsubstituted or substituted with an alkyl group having a carbon number of 1 to 20;

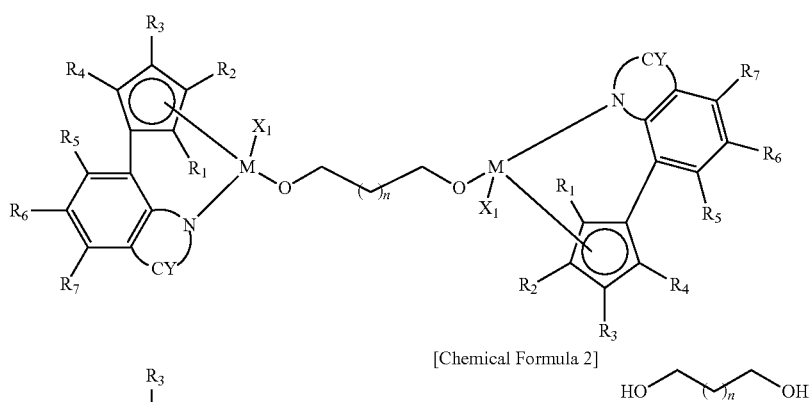

M is titanium (Ti), zirconium (Zr), or hafnium (Hf);
X1 is halogen or an alkyl group having a carbon number of 1 to 20; and
n is an integer of 0 to 10.

2. The dinuclear metallocene compound according to claim 1, wherein the compound of the Chemical Formula 1 is represented by the following structures:

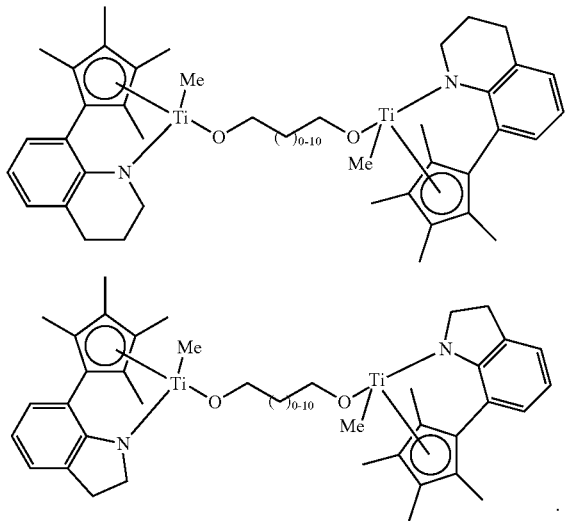

3. A method for preparing a dinuclear metallocene compound represented by the following Chemical Formula 1, comprising the step of reacting a compound represented by the following Chemical Formula 2 with a compound represented by the following Chemical Formula 3:

[Chemical Formula 1]

[Chemical Formula 2]

[Chemical Formula 3]

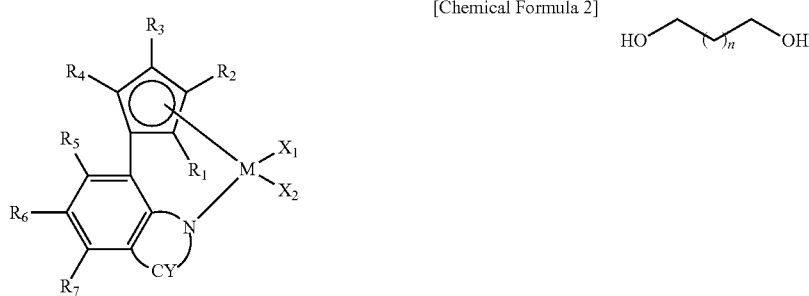

in the Chemical Formulae 1, 2 and 3,
R1 to R7 are independently hydrogen, an alkyl group having a carbon number of 1 to 20, or an aryl group having a carbon number of 6 to 20;

CY is a pentagonal or hexagonal aliphatic or aromatic ring containing nitrogen, unsubstituted or substituted with an alkyl group having a carbon number of 1 to 20;

M is titanium (Ti), zirconium (Zr), or hafnium (Hf);

X1 and X2 are halogen or an alkyl group having a carbon number of 1 to 20; and n is an integer of 0 to 10.

4. The method for preparing a dinuclear metallocene compound according to claim 3, wherein the step of reacting the compound represented by the Chemical Formula 2 with the compound represented by the Chemical Formula 3 is conducted by stirring at a temperature of −30 to 25° C.

5. The method for preparing a dinuclear metallocene compound according to claim 3, wherein the step of reacting the compound represented by the Chemical Formula 2 with the compound represented by the Chemical Formula 3 is conducted in MTBE (methyl tertiary-butyl ether), or toluene solvent.

* * * * *